(12) United States Patent
Schick et al.

(10) Patent No.: US 10,274,482 B2
(45) Date of Patent: Apr. 30, 2019

(54) RARE METALS AS COMPONENTS OF COATINGS IN DIAGNOSTIC TEST ELEMENTS AND METHODS OF DETERMINING AN AMOUNT/QUALITY OF DRIED COMPOSITIONS IN SUCH COATINGS

(71) Applicant: Roche Diabetes Care, Inc., Indianapolis, IN (US)

(72) Inventors: Wolfgang Schick, Mannheim (DE); Alexander Ibach, Buehl (DE); Yilmaz Isgoeren, Ludwigshafen (DE); Kai Kuellmer, Koenigstein im Taunus (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 173 days.

(21) Appl. No.: 15/213,710

(22) Filed: Jul. 19, 2016

(65) Prior Publication Data

US 2016/0356765 A1    Dec. 8, 2016

Related U.S. Application Data

(63) Continuation of application No. PCT/EP2015/052280, filed on Feb. 4, 2015.

(30) Foreign Application Priority Data

Feb. 5, 2014   (EP) ..................... 14153951

(51) Int. Cl.
*G01N 33/52*     (2006.01)
*G01N 33/20*     (2006.01)
(Continued)

(52) U.S. Cl.
CPC .......... *G01N 33/525* (2013.01); *G01N 33/20* (2013.01); *G01N 33/553* (2013.01); *H01J 49/105* (2013.01); *G01N 2033/0096* (2013.01)

(58) Field of Classification Search
CPC .... G01N 33/525; G01N 33/20; G01N 33/553; H01J 49/105
See application file for complete search history.

(56) References Cited

U.S. PATENT DOCUMENTS

| 4,752,567 A | * | 6/1988 | De Brabander | ..... G01N 15/147 348/365 |
| 2003/0044645 A1 | | 3/2003 | Kambe et al. | |

(Continued)

FOREIGN PATENT DOCUMENTS

| EP | 0821233 A2 | 1/1988 |
| EP | 0821234 A2 | 1/1998 |

(Continued)

OTHER PUBLICATIONS

Ene, et al., Determination of Heavy Metals in Soils Using XRF Technique; Rom. Journ.Phys., vol. 55, Nos. 7-8, p. 815-820; Bucharest, 2010.

(Continued)

*Primary Examiner* — Krishnan S Menon
*Assistant Examiner* — Dwan A Gerido

(57) ABSTRACT

Coating compositions are described that include one or more rare metal components, such as rare alkali metal components, as well as diagnostics test elements that incorporate the same. Methods also are described for determining an amount of a dried coating composition in a coat based upon the rare metal components.

13 Claims, 2 Drawing Sheets

(51) Int. Cl.
  *H01J 49/10*  (2006.01)
  *G01N 33/553*  (2006.01)
  *G01N 33/00*  (2006.01)

(56) References Cited

U.S. PATENT DOCUMENTS

| | | |
|---|---|---|
| 2004/0248318 A1 | 12/2004 | Weinberger et al. |
| 2006/0147927 A1 | 7/2006 | Geddes et al. |
| 2007/0203448 A1 | 8/2007 | Melker et al. |
| 2010/0010630 A1 | 1/2010 | Kunze et al. |

FOREIGN PATENT DOCUMENTS

| | | |
|---|---|---|
| JP | 603548 A | 1/1985 |
| JP | 63255659 A | 10/1988 |
| JP | 0213803 A | 1/1990 |
| JP | 1078433 A | 3/1998 |
| JP | 2001141439 A | 5/2001 |
| JP | 2006162627 A | 6/2006 |
| JP | 2009288021 A | 12/2009 |

OTHER PUBLICATIONS

Rizescu, et al.; Heavy metals trace element analysis by X-Ray fluorescence (XRF) spectrometry in eaf dust; International Journal of Energy and Environment; Issue 4, vol. 5, 2011.

* cited by examiner

RARE METALS AS COMPONENTS OF COATINGS IN DIAGNOSTIC TEST ELEMENTS AND METHODS OF DETERMINING AN AMOUNT/QUALITY OF DRIED COMPOSITIONS IN SUCH COATINGS

CROSS-REFERENCE TO RELATED APPLICATIONS

This patent application is a continuation of Int'l Patent Application No. PCT/EP2015/052280 (filed 4 Feb. 2015), which claims priority to and the benefit of EP Patent Application No. 14153951.0 (filed 5 Feb. 2014). Each patent application is incorporated herein by reference as if set forth in its entirety.

TECHNICAL FIELD

This disclosure relates generally to medicine/medical diagnostics, especially manufacturing diagnostic test elements, and more particularly, it relates to using a rare metal component, such as rare alkali metal components, incorporated in a coating composition for determining an amount of dried coating composition in a coat of such test elements.

BACKGROUND

Coating processes are used in many areas of the art. In particular, the manufacture of diagnostic test elements useful in measuring biological analytes such as blood glucose require generating different layer films on a solid support. Theses layers are obtained by a coating process where one or more coating compositions are applied to the solid support. Typical diagnostic test elements and coating processes for generating the same are described in, for example, DE Patent Application Publication Nos. 196 29 656 and 196 29 657, Int'l Patent Application Publication No. WO 2010/052306, and EP Patent No. 0 821 234.

However, it is decisive for reliably working diagnostic test elements that the quality of the coat can be assured. To this end, it is necessary to characterize the coat (i.e. the layers) by determining the amount of dried coating composition that forms the coat. Such characterizing is required to assess the quality of the coat in the context of desired specifications.

Currently, the amount of dried coating composition applied to a solid support is determined by differential weighing (i.e., by weighing the amount of coating composition prior and after application). Thereby, the amount of coating composition that has been applied can be calculated. Moreover, the amount of dried coating composition is subsequently determined by calculating the sum of the amounts of the solid components of the composition.

Differential weighing also may be used to determine the applied dried coating composition directly. To this end, the solid support with the coat of dried coating composition is weighed first. Afterwards, the dried coat is completely removed from the solid support (e.g., by ultrasound treatment), and the solid support without the coat is weighed again. The determined difference of the weights represents the amount of dried coating composition applied as a coat to the solid support.

Likewise, the amount of dried coating composition in a coat can be determined by infrared (IR) spectroscopic techniques or can be determined with heavy elements by X-ray fluorescence (for determining heavy elements by X-ray fluorescence, see, Rizescu (2001) Int'l J. Energ. Environ. 4:503-513; and Ene (2010) Rom. J. Phys. 55:815-820). These techniques, however, are sensitive to matrix effects of the coat or require the addition of high concentrations of heavy elements to the coat.

Thus, there is a need for improved methods of determining the quality of coats and, in particular, of applied dried coating compositions.

BRIEF SUMMARY

The technical problem underlying the present disclosure can be regarded as providing means for and methods of complying with the aforementioned needs. Accordingly, the present disclosure relates, in general, to using rare metal components in coating compositions for determining an amount of dried coating composition in a coat.

For example, coating compositions for forming a coat are provided that can include a rare metal component, especially a rare alkali metal component. In some instances, the rare metal component can be Cs, Fr, Li, or Rb atoms or ions. In other instances, the rare metal component can be CsCl, FrCl, LiCl or RbCl. Alternatively, the rare metal component can be CsF, FrF, LiF or RbF, or CsBr, FrBr, LiBr or RbBr, or Csl, Frl, Lil or Rbl, or CsAt, FrAT, LiAt or RbAt. Alternatively still, the rare metal component can be CsOH, FrOH, LiOH or RbOH. In certain instances, the rare metal component is LiOH or RbOH.

In some instances, the rare metal component is in a coating composition in a pre-defined amount.

In some instances, the rare metal component does not react with other components of the coating composition.

In addition to the coating compositions, diagnostic test elements are provided that can include a coat having at least a detection layer or a reaction layer, where the coat includes at least one dried coating composition as described herein.

In some instances, the coat is a detection layer or a reaction layer. In certain instances, the detection layer or the reaction layer is included as a component of the diagnostic test element.

In view of the foregoing, methods are provided for determining an amount of a dried coating composition in a coat. The methods can include dissolving the coat comprising the dried coating composition in a solvent, where the coating composition includes a rare metal component, and where the solvent includes an internal standard for the rare metal component.

The methods also can include detecting an amount of the rare metal component. In some instances, mass spectroscopy can be used to detect the amount of the rare metal component, such as inductively-coupled plasma mass spectrometry (ICP-MS).

The methods also can include determining an amount of the dried coating composition in the coat based on the detected amount of the rare metal component.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 2A shows an analysis of detection layers on different test elements. FIG. 2B is a scale-up of FIG. 2A in the range between 8.00 mg/m$^2$ and 9.00 mg/m$^2$. Numbering 1-1, 1-2, and 1-3 for the three test pieces of the first pre-cut blank, 2-1, 2-2, 2-3 for the three test pieces of the second pre-cut blank, and 3-1, 3-2, and 3-3 for the three pieces of the third pre-cut blank.

Corresponding reference characters indicate corresponding parts throughout the several views of the drawings.

Figure 1:
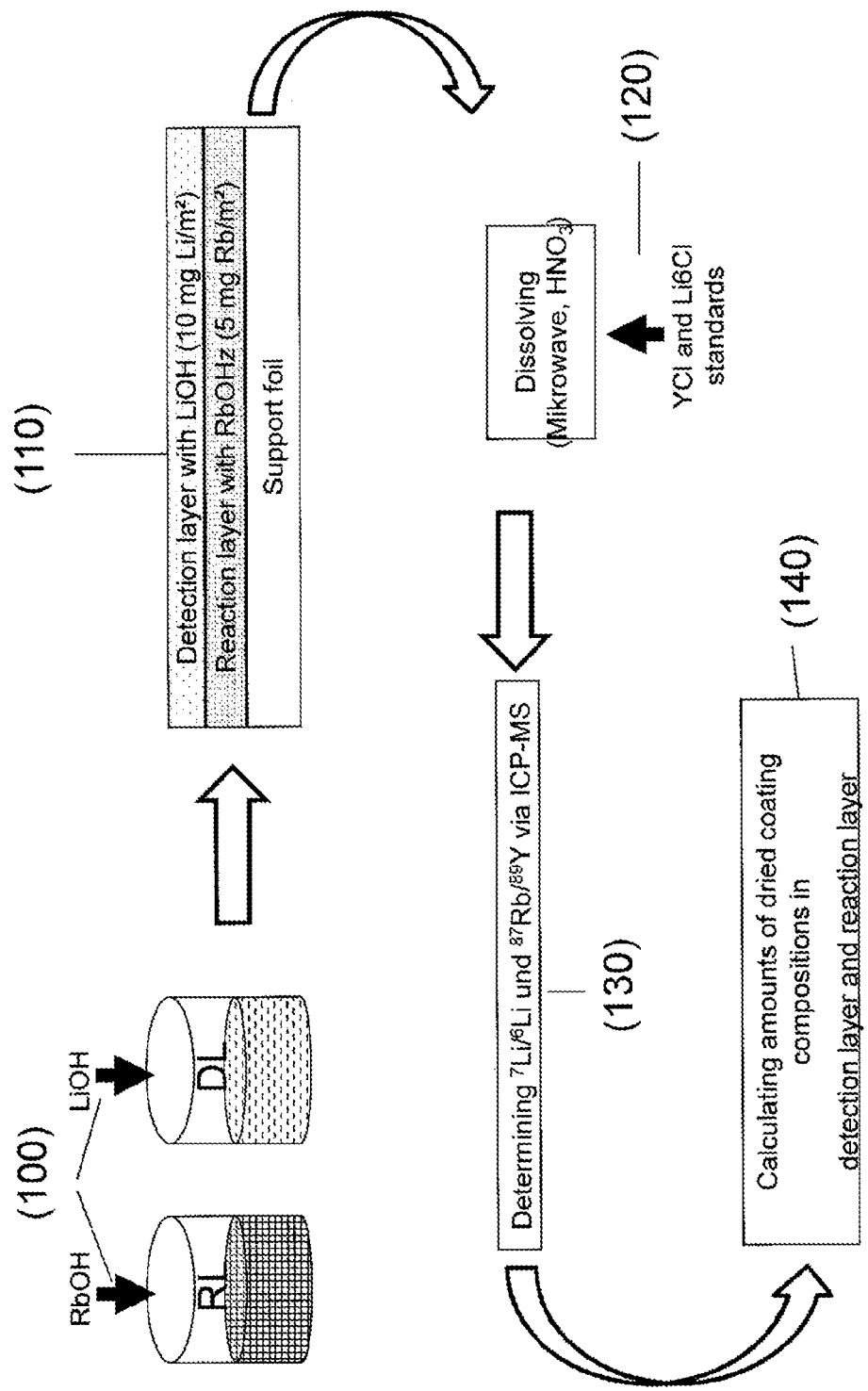
FIG. 1 shows a schematic drawing of an exemplary method as described herein. Coating compositions for detection and reaction layers are generated with rare alkali metal components as key components. An area of a test field is dissolved, and an internal standard for the included key component (i.e., the rare alkali metal component) is added. Subsequently, the amount/content of rare alkali metal atoms or ions is detected by mass spectroscopy, such as ICP-MS. Based on the content of rare alkali metal component, the amount of applied dried coating composition is calculated/determined.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The coatings, diagnostic test elements, and methods now will be described more fully hereinafter with reference to the accompanying drawings, in which some, but not all embodiments of the inventive concept are shown. Indeed, the coatings, diagnostic test elements, and methods may be embodied in many different forms and should not be construed as limited to the embodiments set forth herein; rather, these embodiments are provided so that this disclosure will satisfy applicable legal requirements.

Likewise, many modifications and other embodiments of the coatings, diagnostic test elements, and methods described herein will come to mind to one of skill in the art to which the disclosure pertains having the benefit of the teachings presented in the foregoing descriptions and the associated drawings. Therefore, it is to be understood that the coatings, diagnostic test elements, and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the coatings, diagnostic test elements, and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

The present disclosure relates to using one or more rare metal components in coating compositions for determining an amount of such dried coating compositions in a coat.

It has been found in the studies underlying the present disclosure that rare metal components, such as hydroxides or salts of the rare metals, can be used as key components in pre-defined amounts in coating compositions, especially rare alkali metal components. Based on these rare metal component-containing coating compositions, the amount of dried coating composition in a coat (e.g., a reaction layer or detection layer in a diagnostic test element) can be precisely determined. Since the key components serve as detectable labels for the coat, it will be understood that the rare metal atom or ion of the rare metal component is not introduced from components other than the key component or by contaminations. Rare metal components, especially rare alkali metal components, are particularly well suited as key components in detection or reaction layers of diagnostic test elements because these components are rather inert with respect to other chemical reactions that need to be carried out in these layers. Advantageously, they do not significantly alter required physical properties such as optical properties of the layers. A further advantage of using rare metal components, in particular rare alkali metal components, as key components is that these rare metal atoms or ions can be detected at very low detection levels (e.g., in the ppb (ng/g) range). To this end, mass spectroscopy such as ICP-MS can be readily used as a detection technique in accordance with the findings underlying the present disclosure. Moreover, isotopes of the rare metals can be used as internal standards for calibration purposes, where a precise and quantitative determination of the amount of rare metal component in a dried coating composition is allowed. In this manner, the quality of coatings, in particular in the field of diagnostic test elements, can be significantly improved.

Coating Compositions

Coating compositions incorporating the inventive concept are provided that can include a rare metal component, especially a rare alkali metal component. Such coating compositions can be used to form a coat having at least a detection layer or a reaction layer and that can be incorporated as a component of a diagnostic test element.

As used herein, "coating composition" means a liquid composition capable of forming a coat upon application onto, for example, a solid support. As used herein, the "coat" is formed by removing the solvent from a coating composition such that a dry layer of coating compositions remain on the solid support as coat. Depending on the desired purpose of the coat, the coating compositions may include various components. However, it will be understood that the coating compositions include a removable solvent, such as an aqueous solvent that can be removed from the coating compositions by heat treating, evaporating, or freeze-drying. Other removable solvents, such as organic solvents, also are contemplated. At the very least, the coating compositions described herein, however, include at least one rare metal component as specified above.

In some instances, the at least one rare metal component is at least one rare alkali metal component. In other instances, the at least one rare metal component is incorporated in a coating composition in pre-defined amounts such that based on the pre-defined amount of the at least rare metal component, the applied coating composition-forming coat can be precisely determined even after removing the solvent. It will be understood that depending on the technique used for applying the coating composition to the support, different amounts may be applied. Even if the same technique is used for applying, the applied amounts may vary from coated support to coated support. Based on the amount of rare metal component determined in the coat, it is possible to compare the amounts of dried coating composition applied to different supports (e.g., as a measure of quality control for the coating process).

As used herein, "rare metal component" means compositions including one or more rare metal atoms or ions. As used herein, "rare" means that the metal ion or atom shall not be present in other components of the coating composition in detectable amounts. Accordingly, it shall be a unique component of the coating composition. Therefore, frequently occurring metal ions that are part of salts used for conventional buffers or the like are not considered to be rare. Examples of rare metals and metal ions include, but are not limited to, heavy metals such as transition metals, metalloids, lanthanides and actinides, and some alkali metals.

Of interest herein are rare heavy metals, especially those having a density of $>5$ g/m$^3$, $>10$ g/cm$^3$, or even about 20 g/m$^3$. Heavy metals having a density of at least 5 g/m$^3$ or more include, but are not limited to, Ac, Ag, Am, As, Au, Bi, Bk, Cd, Ce, Cf, Cm, Co, Cr, Cu, Dy, Er, Es, Eu, Fe, Ga, Gd, Ge, Hf, Hg, Ho, In, Ir, La, Lu, Mn, Mo, Nb, Nd, Ni, Np, Os, Pa, Pb, Pd, Pm, Po, Pr, Pt, Pu, Ra, Re, Rf, Rh, Ru, Sb, Sm, Sn, Ta, Tb, Tc, Te, Th, Tl, Tm, U, V, W, Yb, Zn and Zr. Moreover, it is contemplated that the rare heavy metal atom or ion used in the rare heavy metal component herein is positively charged after ionization in the context of MS analysis. Furthermore, it is contemplated that the rare heavy metal component does not interfere with other components of the coating compositions and their purpose in the coats. For example, for most purposes of coats, non-radioactive heavy metals may be desired.

Of particular interest herein for the rare metal component are rare alkali metal components. As used herein, "rare alkali metal component" means a composition having a rare alkali metal atom or ion. Examples of alkali metals for use with the coating compositions herein include, but are not limited to, sodium (Na) and potassium (K). Moreover, rare alkali metals for use in the coating compositions herein include, but are not limited to, lithium (Li), rubidium (Rb), cesium (Cs), and francium (Fr) atoms or ions. Compositions that may be suitable as rare alkali metal components for the coating compositions herein are salts, hydroxides or organometallic compounds including such rare alkali metal atoms or ions. Particularly envisaged are salts, such as halogen salts, and hydroxides of the rare alkali metals. For example, the rare alkali metal components may be LiCl, RbCl, CsCl, or FrCl. Instead of the chloride (Cl$^-$) anion, any other halide may be used, such as fluoride (F$^-$), bromide (Br$^-$), iodide (I$^-$), or astatide (At$^-$). In this manner, the rare alkali metal components may be LiF, RbF, CsF or FrF, or LiBr, RbBr, CsBr or FrBr, or LiI, RbI, CsI or FrI, or LiAt, RbAt, CsAt or FrAt. Other salt-forming anions can be used as well. Alternatively, the rare alkali metal components may be LiOH, RbOH, CsOH or FrOH. In some instances, LiOH or RbOH are suitable rare alkali metal components.

In some instances, the coating compositions have the rare metal component form a detection layer or a reaction layer of a diagnostic test element, as described in greater detail below. As such, coating compositions that are capable of forming the detection layer or reaction layer typically are an aqueous composition and therefore become contained in the coating compositions. Moreover, the compositions can include suitable solvents for the components that are well known to one of skill in the art. See, e.g., DE Patent Application Publication Nos. 196 29 657 and 196 29 656, and EP Patent Nos. 0 821 234, 1 035 919 and 1 035 920.

Diagnostic Test Elements

Diagnostic test elements incorporating the inventive concept are provided that can include, in principle, a coat having at least one detection layer having a reagent for qualitatively and/or quantitatively detecting an analyte in, for example, a body fluid sample, where the detection layer includes a coating composition having a rare metal component. The test elements also can include a second coat having at least one reaction layer that includes a coating composition having a rare metal component that differs with respect to the rare metal component of the detection layer. In this manner, and as explained in greater detail below, such an arrangement allows one to determine the amount of dried coating composition in different coats using the same analysis (e.g., mass spectroscopy such as ICP-MS).

As used herein, "detection reagent" means a chemical substance or a mixture of chemical substances that, in the presence of the analyte of interest, changes at least one detectable property such as a physically and/or chemically detectable property. In some instances, this property change occurs specifically only in the presence of the analyte to be detected, but not in the presence of other substances.

The at least one property change can be, for example, a change in an optically detectable property, more particularly a color change. Examples of diagnostic test elements having optical detection reagents are well known in the prior art. See, e.g., DE Patent Application Publication Nos. 196 29 656 and 196 29 657, Intl Patent Application Publication No. WO 2010/052306, and EP Patent No. 0 821 234, which describe diagnostic test elements for determining an analyte from whole blood by means of a reagent system present in the test element and which includes a color formation reagent.

Briefly, such diagnostic test elements include a test field with a sample loading side, onto which the sample is added, and a detection side, on which an optically detectable change occurs as a result of the reaction of the analyte with the reagent system. The test field is configured so that any erythrocytes present in a whole blood sample do not reach the detection side. Furthermore, the test field has a transparent slide, a first film layer, and a second film layer applied to the first film layer. The first layer or reaction layer located on the transparent slide is in a moist state and thereby exhibits considerably less light scattering than the second layer lying over it. It includes the detection reagents for detecting the analyte. The first film layer typically includes a filler whose refractive index is close to the refractive index of water, whereas the second layer or detection layer includes a pigment having a refractive index of at least or even >2.0, or even of at least 2.2, at a concentration of at least 25% by weight or even more than 25% by weight, based on the dried second layer. For example, the first layer can include a sodium aluminum silicate ($AlNa_{12}SiO_5$) as filler.

As used herein, "reaction layer" (or "first layer") means a film layer in the test field that includes the reaction reagent(s) for detecting the analyte. Moreover, the layer includes coating compounds containing polymeric film formers, swelling agents and weakly light scattering fillers or no fillers at all. Weakly light fillers have a refractive index that is near to the refractive index of water. Examples of weakly light fillers include, but are not limited to, silicone dioxide, silicates and aluminum silicates.

As used herein, "detection layer" (or "second layer") means a film layer in the test field that includes dispersion-saturated solid components. Typically, the detection layer contains a swelling agent and in any case at least one strongly light scattering pigment. Ideally the refractive index of the at least one pigment in the detection layer should be at least 2.5, such as $TiO_2$. In addition, the detection layer can include non-porous fillers as well as porous fillers. By adding a swelling agent that swells well (i.e., a substance that increases its volume when it takes up water), one not only obtains layers that can be penetrated relatively rapidly by sample liquid but also obtains layers that have good erythrocyte and blood pigment separation properties despite the opening effect of the swelling agent. In this manner, the swelling properties should be such that for a test in which the rate of color formation—such as, for example, of a glucose test reaction—is mainly dependent on penetration of the sample liquid through the layer, the optically detectable reaction is measurable after a maximum of one minute. Examples of swelling agents include, but are not limited to, methyl vinyl ether maleic acid anhydride copolymer, xanthan gum, and methyl vinyl ether maleic acid copolymer. One of skill in the art understands that one or more reaction and/or detection layers may be used in accordance with the diagnostic test elements described herein.

In view of the above, the detection layer of a diagnostic test element can be formed from a coating composition including a first rare metal component, while the reaction layer is formed from a coating composition including a second rare metal component, where the first and the second rare metal components differ with respect to the rare metal atom or ion. It is possible to use the different rare metal components for determining the amount of each in the dried coating composition that includes the detection layer and the reaction layer. In some instances, the at least one rare metal component in the coating composition is at least one rare alkali metal component such as, for example RbOH and LiOH as first and second rare alkali metal components, respectively.

The manufacture of diagnostic test elements including test fields having a multiple layer structure is, in principle, well known to one of skill in the art and are described in, for example, DE Patent Application Publication Nos. 196 29 657 and 196 29 656, and EP Patent No. 0 821 234.

In view thereof, a coating composition for the reaction layer can be applied to the test field on the diagnostic element first. Subsequently, a solvent is removed from the coating composition thereby forming a dry coat being the first layer (i.e., the reaction layer). In a further step, the coating composition for the detection layer can be applied to the first layer. The solvent is again removed thereby forming the second layer (i.e., the detection layer). In either case, the solvent can be removed from the coating composition after applying it to the test field of the diagnostic test element by any technique known for removing solvents including, but not limited to, heat treating, evaporating, and/or freeze-drying.

Methods

Methods incorporating the inventive concept include methods of determining an amount of a dried coating composition in a coat. The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

Briefly, such methods can include steps of: (a) dissolving the coat comprising the dried coating composition in a solvent, where the coating composition includes a rare metal component, and where the solvent includes an internal standard for the rare metal component; (b) detecting an amount of the rare metal component; and (c) determining an amount of dried coating composition in the coat based on the detected amount of the rare metal component.

With respect to the dissolving step, it may be carried out by any suitable means known to one of skill in the art. As used herein, "dissolving the coat" means mobilizing the individual components of the dried coating composition in the coat and bringing them into solution. Typically, the coat or a pre-defined part thereof can be dissolved in an acidic aqueous solution such as a $HNO_3$ solution. Alternatively or additionally, dissolving may include applying physical forces such as, for example, shaking or applying microwave irradiation.

Typically, an internal standard for the rare metal component, in particular a rare alkali metal component, is added in a pre-defined amount once the coat is dissolved. Such a standard may be an isotope of the rare metal or may be a compound containing it. Based on the pre-defined amount of the internal standard, a calibration for different amounts of the rare metal component is feasible.

With respect to the detecting step, it may be carried out by any suitable means known to one of skill in the art. For example, mass spectroscopy can be used to detect an amount of the rare metal component, especially ICP-MS. As such, detecting of the rare metal component, in particular the rare alkali metal component, can be carried out by various detection techniques that allow for a specific quantitative determination of the rare metal atoms or ions comprised in the solution comprising the dissolved coat. In particular, spectroscopy techniques are suitable for determining the rare metal atoms or ions based on their physical and/or chemical properties. Nevertheless, other techniques are also encompassed according to the present invention. In particular, mass spectroscopy techniques, such as ICP-MS, give particular favorable results when applied in the methods herein. Techniques such as infrared (IR) spectroscopy are dependent on matrix effects or, in the case of, for example, X-ray fluorescence analysis, require heavy key-components in rather high concentrations to be present in the coating composition.

With respect to the determining step, it may be carried out by any suitable means known to one of skill in the art. For example, the amount of dried coating composition comprised in the coat can be determined based on the detected amount of the rare metal component. To this end, the determined amount is compared with the pre-defined amounts of internal standard so that the amount can be calculated quantitatively.

In some instances, two coats having a first and a second dried coating composition, respectively, are dissolved in at least one solvent, where the first coating composition includes a first rare metal component, where the second coating composition includes a second rare metal component, and where the at least one solvent includes at least one internal standard for the first rare metal component and/or for the second rare metal component, thereby determining the absolute and/or relative amount of the first and the second dried coating composition in the two coats based on the detected amount of the first and the second rare metal component.

Thus, the method encompasses dissolving two different coats, such as a reaction and a detection layer of a diagnostic test element, whereby the coats include different rare metal components. The methods herein thus allow for determining the amount of coating composition in each of the different coats within one process since the one coating composition is represented by a first metal component while the other coating composition is represented by a second rare metal component differing from the first one with respect to the rare metal atom or ion. In this manner, the methods herein allow for determining the relative amounts as well as the absolute amounts of the coating compositions in different layers in relation to each other. By comparing the absolute or relative amounts in two different layers, ratios may be calculated and established for quality control purposes in the coating process. In some instances, the rare metal components are rare alkali metal components.

As used herein, "amount" means an absolute amount or a relative amount (i.e., a concentration of the components in a certain volume). It will be understood that based on the amount of dried coating composition, other parameters characterizing a coat such as its thickness or its weight can be calculated as well.

EXAMPLES

The inventive concept will be more fully understood upon consideration of the following non-limiting examples, which are offered for purposes of illustration, not limitation.

Example 1

Manufacturing Diagnostic Test Elements with Coating Compositions Including Rare Alkali Metals as Key Components Coating compositions for detection and reaction layers were generated essentially as described in DE Patent Application Publication Nos. 196 29 657 and 196 29 656, as well as EP Patent 0 821 234.

In addition, however, LiOH was added to the detection layer coating composition in an amount such that the final coat shall comprise 10 mg $Li^+/m^2$. RbOH was added to the reaction layer coating composition in an amount such that the final coat was 10 mg $Rb^+/m^2$. To this end, RbOH was added in a concentration of 0.01 g/100 g coating composition to the reaction layer coating composition, while LiOH was added in a concentration of 0.06 g/100 g coating composition to the detection layer coating composition.

Example 2

Measuring Precise Amounts of Dried Coating Compositions in Coatings Using ICP-MS A 1 $cm^2$ area of a test field of a diagnostic test element manufactured as indicated in Example 1 was dissolved in $HNO_3$ and treated in a microwave until the layers and the support matrices were entirely dissolved. $Y^{89}Cl$ and $Li^6Cl$ were added in predefined amounts as internal calibration standards to different samples. ICP-MS was carried out to determine the ratios of $Li^7/Li^6$ and $Rb^{86}/Y^{87}$. The amount of dried composition in the detection and reaction layer was calculated based on the amounts used for generating the coating compositions, and the ratios of the isotopes determined by ICP-MS (see, FIG. 1).

Figure 2A:
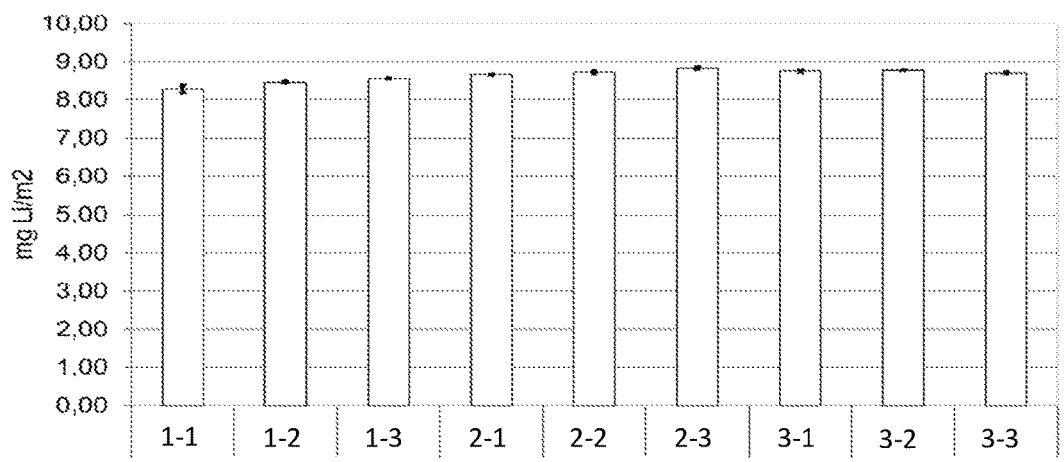
FIGS. 2A-B show ICP-MS analyses for determining an amount of lithium (Li) ions present in a coat obtained from a lithium hydroxide (LiOH) containing coating composition.
Figure 2B:
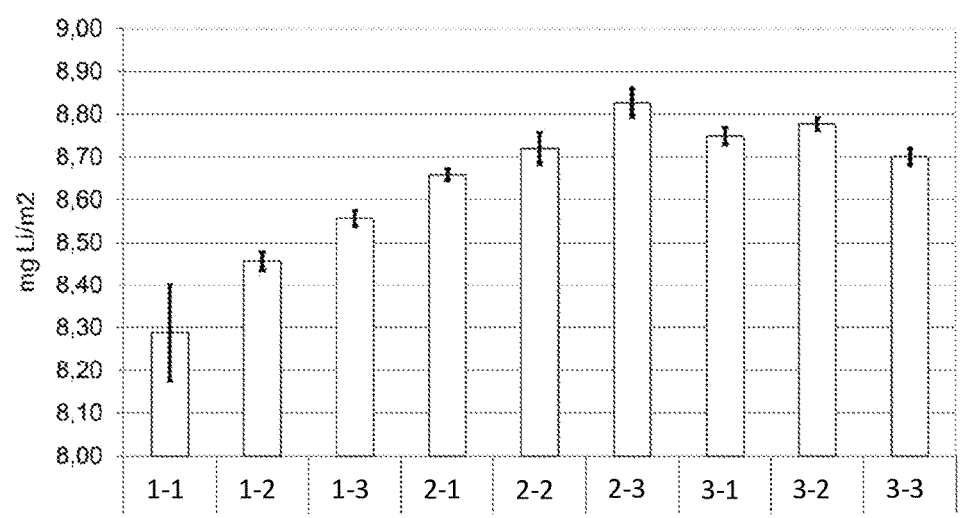

The results obtained for different test elements are shown in FIG. 2A. In particular, FIG. 2B shows that minor differences in the amount of dried coating composition can be determined based on the Li ions as key components by ICP-MS. Three (3) test pieces of three pre-cut blanks were investigated (numbering 1-1, 1-2, and 1-3 for the three test pieces of the first pre-cut blank, 2-1, 2-2, 2-3 for the three test pieces of the second pre-cut blank, and 3-1, 3-2, and 3-3 for the three pieces of the third pre-cut blank).

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

LISTING OF REFERENCE NUMBERS

100 key components
110 test field
120 dissolving step
130 detecting step
140 calculating/determining step

The invention claimed is:
1. A method of determining an amount of a dried coating composition in at least one coat, the method comprising the steps of:
   a) dissolving the at least one coat comprising the dried coating composition in a solvent, wherein the dried coating composition comprises a rare metal component, and wherein the solvent comprises an internal standard for the rare metal component;
   b) detecting an amount of the rare metal component in the at least one dissolved coat; and c) determining the amount of the dried coating composition in the at least one coat based on the detected amount of the rare metal component.

2. The method of claim 1, wherein the rare metal component is a rare alkali metal component.

3. The method of claim 1, wherein the rare metal component does not react with other components of the dried coating composition.

4. The method of claim 2, wherein the rare alkali metal component comprises a lithium, rubidium, or cesium ion.

5. The method of claim 1, wherein the rare metal component is a rare metal hydroxide or salt.

6. The method of claim 1, wherein the rare metal component is present in a pre-defined amount in the dried coating composition.

7. The method of claim 1, wherein the at least one coat is a detection layer or a reaction layer.

8. The method of claim 7, wherein the detection layer or the reaction layer comprises a component of a diagnostic test element.

9. The method of claim 1, wherein the detecting step comprises mass spectroscopy.

10. The method of claim 9, wherein the mass spectroscopy is inductive coupled mass spectroscopy (ICP-MS).

11. The method of claim 1, wherein the dissolving step comprises an acidic treatment, a microwave treatment, or a combination thereof.

12. The method of claim 1, wherein the internal standard is an isotope-enriched rare metal component.

13. The method of claim 1, wherein the at least one coat is two coats, wherein one coat comprises a first dried coating composition and the other coat comprises a second dried coating composition, wherein the two coats are dissolved in at least one solvent, wherein the first coating composition comprises a first rare metal component, wherein the second coating composition comprises a second rare metal component, and wherein the at least one solvent comprises at least one internal standard for the first rare metal component and/or for the second rare metal component, thereby determining the absolute and/or relative amount of the first and said second dried coating compositions based on the detected amount of the first and the second rare metal components.

* * * * *